United States Patent
Yu et al.

(10) Patent No.: US 9,841,387 B2
(45) Date of Patent: Dec. 12, 2017

(54) INSPECTION METHOD AND DEVICE

(71) Applicant: Test Research, Inc., Taipei (TW)

(72) Inventors: Liang-Pin Yu, Taipei (TW); Chia-Ho Yen, Taoyuan (TW); Hao-Kai Chou, Taichung (TW); Chun-Ti Chen, Taipei (TW); Meng-Kun Lee, Taipei (TW)

(73) Assignee: Test Research, Inc., Taipei (TW)

( * ) Notice: Subject to any disclaimer, the term of this patent is extended or adjusted under 35 U.S.C. 154(b) by 5 days.

(21) Appl. No.: 14/986,718

(22) Filed: Jan. 3, 2016

(65) Prior Publication Data

US 2017/0023494 A1    Jan. 26, 2017

Related U.S. Application Data

(60) Provisional application No. 62/195,314, filed on Jul. 22, 2015.

(51) Int. Cl.
*G06K 9/00* (2006.01)
*G01N 23/04* (2006.01)
*G01B 15/04* (2006.01)

(52) U.S. Cl.
CPC ............ *G01N 23/04* (2013.01); *G01B 15/04* (2013.01); *G01B 2210/56* (2013.01); *G06K 9/00* (2013.01)

(58) Field of Classification Search
CPC ......... G06T 7/521; G06T 7/571; G06T 11/00; G06T 7/0012; G06T 2207/10072; G06T 2207/10116; G06T 7/11; G06T 7/187; G06T 2200/04; G06T 2207/10136; G06T 7/33; G06T 7/73; G06T 2207/30016; G06T 2207/30104; G06T 7/68; H05K 3/3436; H05K 1/0269; B23K 31/12; G01N 2223/419; G01N 23/046; G01N 23/201; G01N 2223/33; G01N 2223/401; G01N 23/04; G01R 31/046; G01R 31/048; G01R 31/2812; G01R 33/4812; A61B 6/12; A61B 6/481; A61B 6/501; A61B 6/504; A61B 2090/392; A61B 6/4258; A61B 8/0833; A61B 8/4245; A61B 2092/367;
(Continued)

(56) References Cited

U.S. PATENT DOCUMENTS 4,920,491 A * 4/1990 Eberhard ............ G01N 23/046 378/901
6,021,213 A * 2/2000 Helterbrand .............. G06T 7/11 382/128
(Continued)

FOREIGN PATENT DOCUMENTS

JP    2006226875 A    8/2006
JP    2007017304 A    1/2007
(Continued)

*Primary Examiner* — Aklilu Woldemariam
(74) *Attorney, Agent, or Firm* — CKC & Partners Co., Ltd.

(57) ABSTRACT

An inspection method is provided herein. The inspection method is adapted for an inspection device. The inspection method includes: optically scanning an examining target for generating a scanned image; reconstructing the scanned image for a reconstructed volume; adjusting a slicing direction associated with the examining target for slicing the reconstructed volume into a sliced image; inspecting the sliced image for analyzing one or more features of the examining target; and outputting an inspection result of the examining target.

14 Claims, 8 Drawing Sheets

(58) Field of Classification Search
CPC ... A61B 8/5223; A61B 8/5246; A61B 6/5235;
A61B 6/5247; G01S 15/8993; Y10S
378/901; G01T 1/1644; A61N 5/0601;
G01V 5/0025
USPC ........ 382/128, 129, 130, 131, 132, 145, 147
See application file for complete search history.

(56) References Cited

U.S. PATENT DOCUMENTS

| | | | | |
|---|---|---|---|---|
| 6,122,344 | A * | 9/2000 | Beevor | G01N 23/201 378/57 |
| 6,738,450 | B1 * | 5/2004 | Barford | G01N 23/04 378/58 |
| 6,996,265 | B1 | 2/2006 | Patnaik | |
| 8,351,682 | B2 | 1/2013 | Hayashi et al. | |
| 2003/0035576 | A1 | 2/2003 | Roder | |
| 2004/0054248 | A1 * | 3/2004 | Kimchy | A61B 5/055 600/3 |
| 2005/0008115 | A1 * | 1/2005 | Tsukagoshi | A61B 6/032 378/4 |
| 2005/0104585 | A1 * | 5/2005 | Bilik | G01N 27/9033 324/240 |
| 2005/0207655 | A1 * | 9/2005 | Chopra | G06T 7/0004 382/218 |
| 2006/0196914 | A1 | 9/2006 | Hiramatsu et al. | |
| 2007/0009086 | A1 | 1/2007 | Yoshino | |
| 2007/0053489 | A1 * | 3/2007 | Lu | G01N 23/04 378/62 |
| 2007/0189460 | A1 * | 8/2007 | Buck | G01N 23/04 378/146 |
| 2008/0021502 | A1 * | 1/2008 | Imielinska | A61B 6/032 607/1 |
| 2012/0230563 | A1 * | 9/2012 | Vik | A61B 6/032 382/128 |
| 2012/0294508 | A1 | 11/2012 | Wada et al. | |
| 2013/0053679 | A1 * | 2/2013 | Owen | A61B 6/032 600/411 |
| 2013/0230144 | A1 * | 9/2013 | Tan | G01N 23/046 378/63 |
| 2013/0262028 | A1 * | 10/2013 | De Prisco | G01N 33/24 702/156 |

FOREIGN PATENT DOCUMENTS

| | | |
|---|---|---|
| JP | 2007114150 A | 5/2007 |
| JP | 2007121082 A | 5/2007 |
| JP | 2009014693 A | 1/2009 |
| JP | 2009063387 A | 3/2009 |
| JP | 2009092610 A | 4/2009 |
| JP | 2010271165 A | 12/2010 |
| JP | 2011080944 A | 4/2011 |
| TW | 200846655 A | 12/2008 |
| TW | 200935074 A | 8/2009 |
| WO | 0135051 A2 | 5/2001 |
| WO | 0135051 A3 | 5/2001 |

* cited by examiner

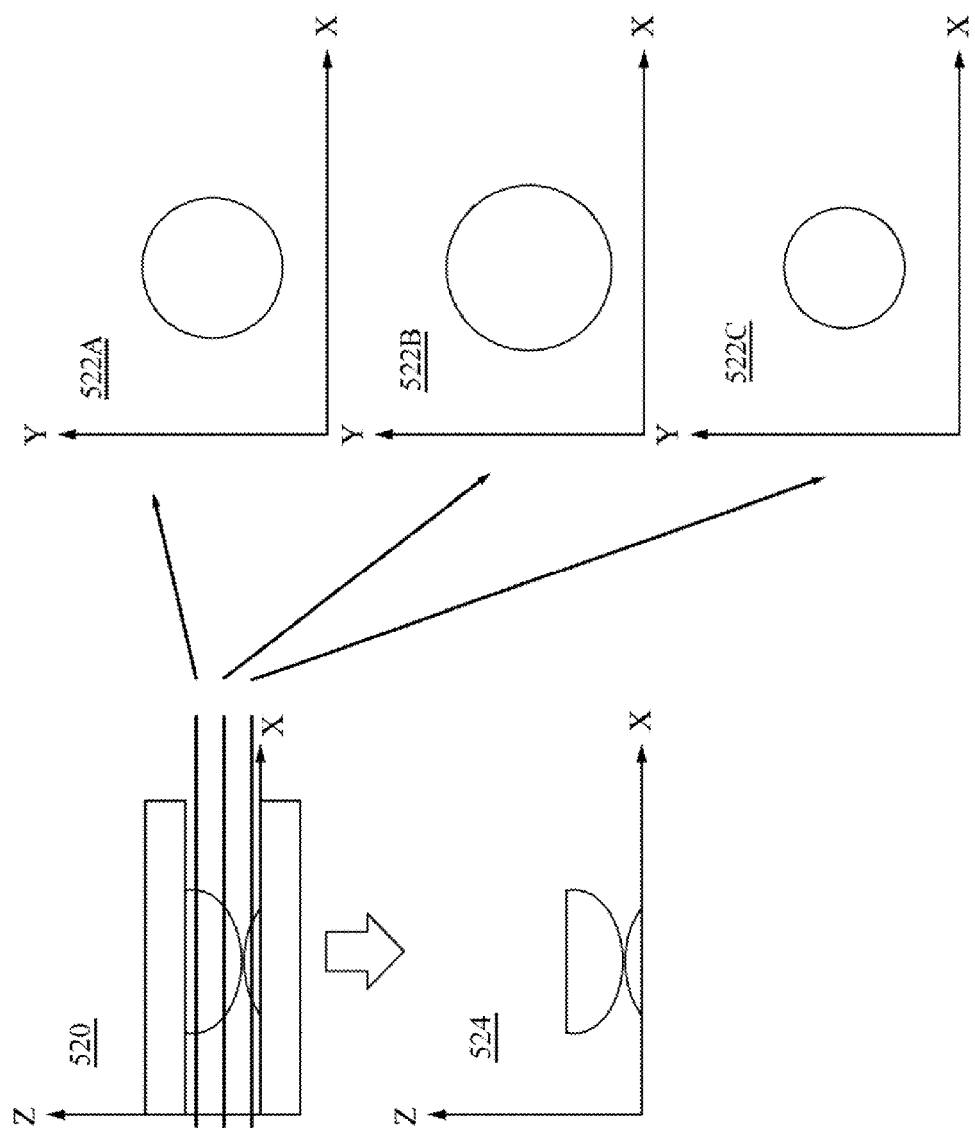

INSPECTION METHOD AND DEVICE

RELATED APPLICATIONS

This application claims priority to U.S. Provisional Application Ser. No. 62/195,314, filed Jul. 22, 2015, which is herein incorporated by reference.

BACKGROUND

Field of Invention

The present invention relates to inspection technique. More particularly, the present invention relates to method and device for inspection.

Description of Related Art

Conventional inline 3D AXI (Advanced eXtensible Interface) equipments usually use horizontally sliced images in the inspection algorithm. A scanned image of examining target may be captured for inspection.

In operation, if the examining target has no significant feature in the horizontal slice, it could lead to poor efficiency of inspection algorithm, and therefore the inspection result may be difficult to be reviewed in a repair station.

SUMMARY

In one aspect, the present disclosure is related to an inspection method including the following steps: optically scanning an examining target for generating a scanned image; reconstructing the scanned image for a reconstructed volume; adjusting a slicing direction associated with the examining target for slicing the reconstructed volume into a sliced image, wherein the slicing direction comprises a non-horizontal slicing direction; inspecting the sliced image for analyzing one or more features of the examining target; and outputting an inspection result of the examining target.

In another aspect, the present disclosure is related to an inspection device. The inspection device includes a scanning device and a computing device. The scanning device is configured to optically scan an examining target for generating a scanned image. The computing device is connected with the scanning device and comprises a processing unit and a storage unit. The processing unit is configured to execute the following instructions: reconstructing the scanned image for a reconstructed volume; adjusting a slicing direction associated with the examining target for slicing the reconstructed volume into a sliced image, wherein the slicing direction comprises a non-horizontal slicing direction; inspecting the sliced image for analyzing one or more features of the examining target; and outputting an inspection result of the examining target to an output device in which the storage unit is configured to store the scanned image, the reconstructed volume and the sliced image.

By applying the techniques disclosed in the present disclosure, a non-horizontal slice of an examining target can provide some characteristics and significant features of the examining target. Therefore, the inspection performance may be improved and the inspection result may be more easily reviewed in repair station.

These and other features, aspects, and advantages of the present invention will become better understood with reference to the following description and appended claims.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIG. 5 is a schematic diagram illustrating a reconstructed volume and corresponding sliced images according to one embodiment of the present disclosure;

DETAILED DESCRIPTION

Figure 1:
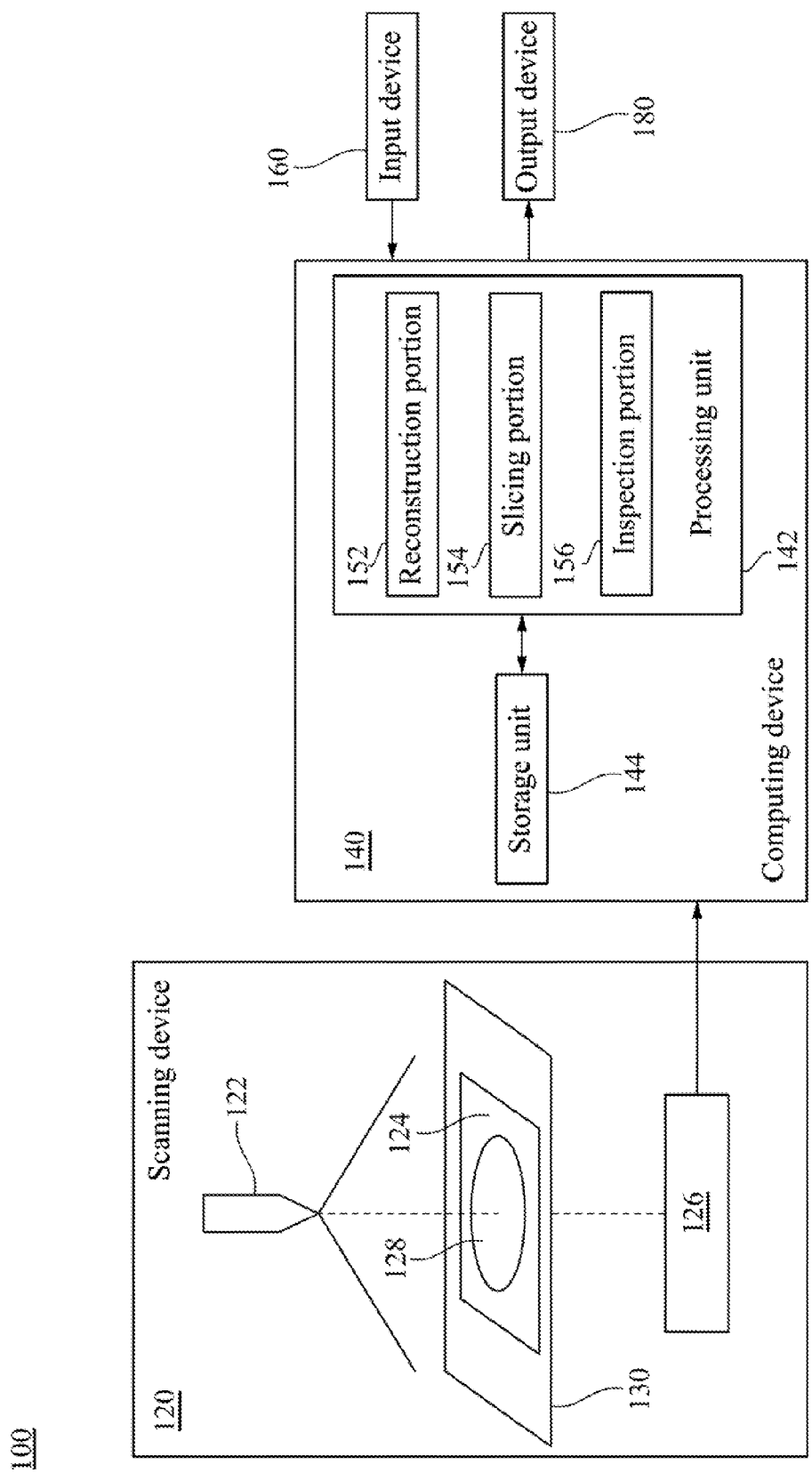
FIG. 1 is a schematic diagram illustrating an inspection device according to one embodiment of the present disclosure.

Reference will now be made in detail to the present embodiments of the invention, examples of which are illustrated in the accompanying drawings. Wherever possible, the same reference numbers are used in the drawings and the description to refer to the same or like parts.

FIG. 1 is a schematic diagram illustrating an inspection device 100 according to one embodiment of the present disclosure. The inspection device 100 comprises a scanning device 120, a computing device 140, an input device 160 and an output device 180. The scanning device 120 further includes an X-ray generator 122, a substrate holding unit 124 and an X-ray detector 126. The computing device 140 comprises a processing unit 142 and a storage unit 144.

The substrate holding unit 124 holds an examining target 128 to be inspected. The X-ray generator 122 generates X-ray. The X-ray is controlled by, for example, an X-ray source control mechanism, and irradiates the examining target 128. The examining target 128 is moved by the substrate holding unit 124, and is arranged between the radiation ray generator 122 and the X-ray detector 126.

The X-ray detector 126 is for detecting the X-ray outputted from the X-ray generator 122 and transmitted through the examining target 128. The X-rays passing through the examining target 128 are photographed as an image by the X-ray detector 126. Hence, a "scanned image" of the examining target 128 is generated by the X-ray detector 126. In some embodiments, the X-ray detector 126 may be an image intensifier tube or a FPD (flat panel detector), but not limited thereto. The scanned image is sent to the computing device 140 and stored in the storage unit 144.

The computing device 140 includes the processing unit 142 and the storage unit 144. The processing unit 142 further includes a reconstruction portion 152, a slicing portion 154 and an inspection portion 156.

In order to efficiently inspect the examining target 128, the inspection device 100 extracts some features from the examining target 128. The processing unit 142 controls the reconstruction portion 152 to receive the scanned image outputted from the X-ray detector 126 and generates a "reconstructed volume" including, for example, a three-dimensional shape of the examining target 128. In some applications, the reconstructed volume is also referred as "3D image". In some embodiments, the method of reconstructing the scanned image for the reconstructed volume comprises shift-and-add or CT (computed tomography), but not limited thereto.

In addition, the processing unit 142 further controls the slicing portion 154 to slice the reconstructed volume into a "sliced image". In some embodiments, the sliced image is a horizontal, vertical or arbitrary cross-section cut out from the reconstructed volume. The slicing direction of the sliced image is determined according to characteristics of the examining target 128, which will be described later. The processing unit 142 then controls the inspection portion 156 to inspect the sliced image for analyzing one or more features of the examining target 128 so as to output the inspection results of the examining target 128 to the output device 180.

The input device 160 is capable of accepting instructions and the like from user. The output device 180 is capable of outputting inspection results, scanned image, reconstructed volume, sliced image and the like to outside of the inspection device 100. In some embodiments, the input device 160 is a keyboard, and the output device 180 is a monitor.

In some embodiments, the computing device 140 is a PC (Personal Computer). The storage unit 144 is configured to store the scanned image, reconstructed volume, sliced image, inspection result and the like. The storage unit 144 merely needs to be able to store data, and is configured by a storage device such as RAM (Random Access Memory) and HDD (Hard Disc Drive), but not limited thereto.

In some embodiments, the inspection portion 156 inspects the symmetry of the slice image and outputs an abnormal result when the symmetry of the sliced image is under a predetermined threshold value.

Figure 2B:
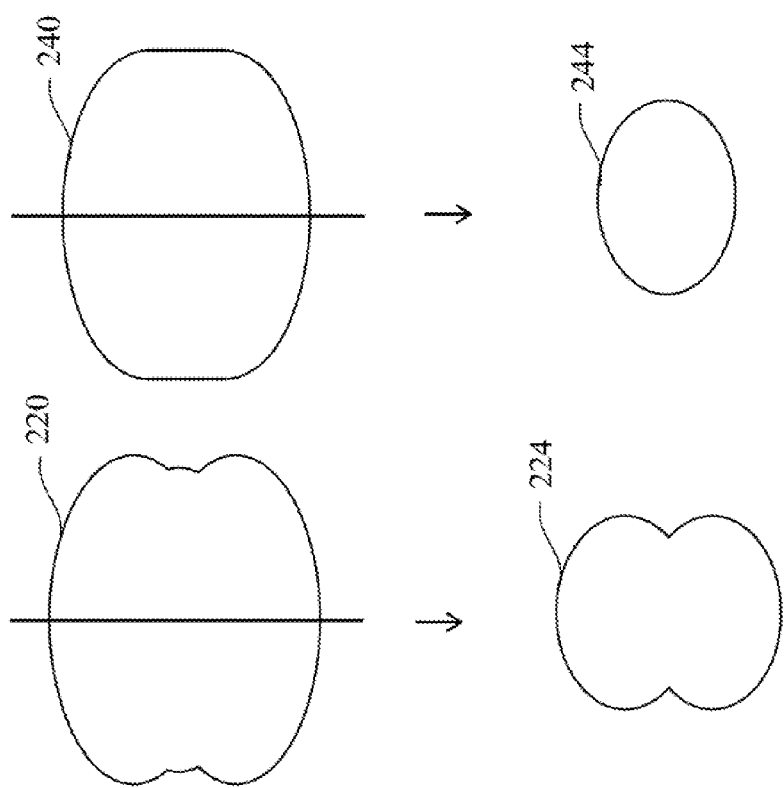
FIG. 2B is a schematic diagram illustrating reconstructed volumes and corresponding sliced images according to one embodiment of the present disclosure.
Figure 2A:
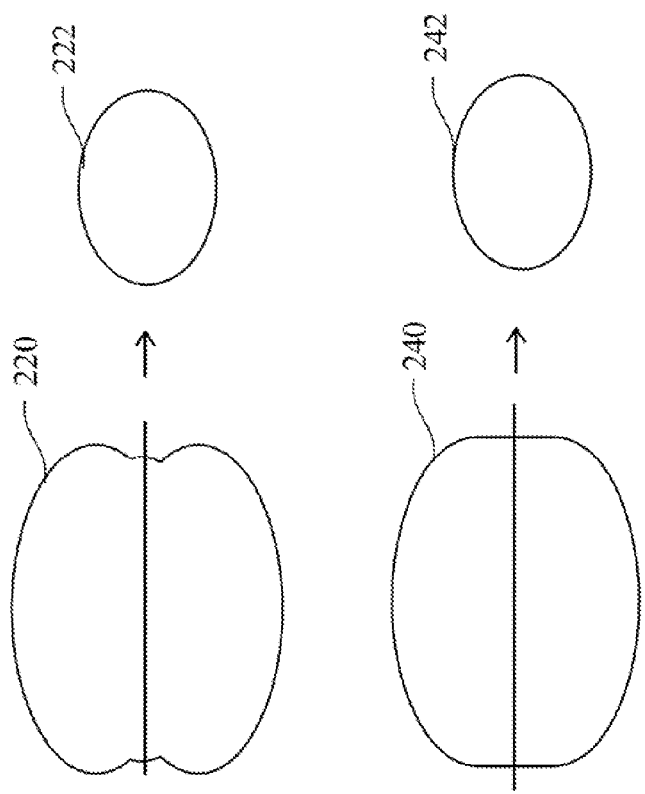
FIG. 2A is a schematic diagram illustrating reconstructed volumes and corresponding sliced images according to one embodiment of the present disclosure.

FIG. 2A is a schematic diagram illustrating reconstructed volumes and corresponding sliced images according to one embodiment of the present disclosure. In this embodiment, reconstructed volume 220 corresponds to a solder ball with head-in-pillow (HIP) defect, and reconstructed volume 240 corresponds to a solder ball without HIP defect. In addition, sliced image 222 is the horizontal slice of the reconstructed volume 220, and sliced image 242 is the horizontal slice of the reconstructed volume 240. As shown in FIG. 2A, it is hardly to distinguish HIP defect from a normal solder ball by the horizontal slices, since there is no clue in the horizontal slice.

FIG. 2B is a schematic diagram illustrating reconstructed volumes and corresponding sliced images according to one embodiment of the present disclosure. In this embodiment, reconstructed volume 220 corresponds to a solder ball with head-in-pillow (HIP) defect, and reconstructed volume 240 corresponds to a solder ball without HIP defect. In addition, sliced image 224 is the vertical slice of the reconstructed volume 220, and sliced image 244 is the vertical slice of the reconstructed volume 240.

Since the sliced image 224 and the sliced image 244 contain some vertical characteristics or information, so as to make HIP defect becomes more apparently. In other words, when the inspection device 100 inspects HIP defect of the examining target 128, the processing unit 142 may control the slicing portion 154 to cut a vertical slice of the reconstructed volume so as to speed up the determination of HIP defect.

Figure 3:
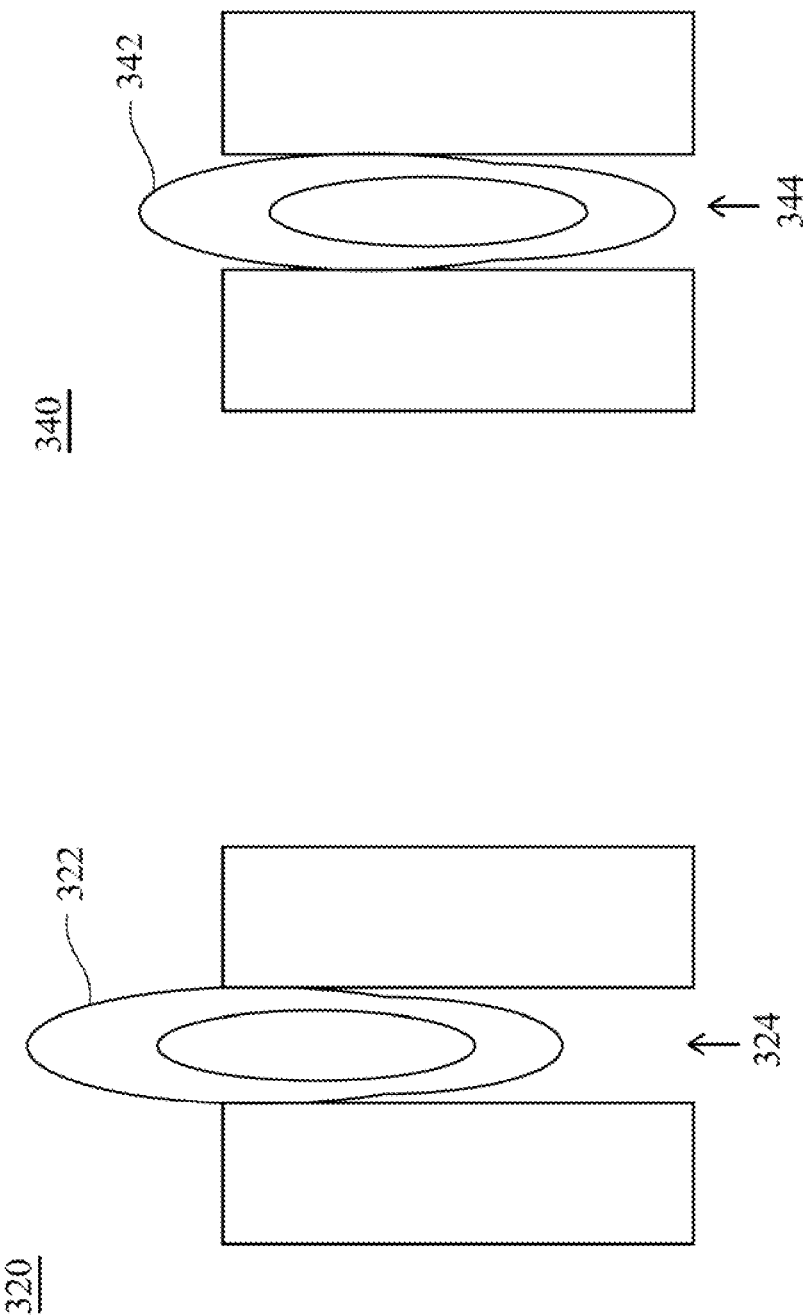
FIG. 3 is a schematic diagram illustrating sliced images according to one embodiment of the present disclosure.

FIG. 3 is a schematic diagram illustrating sliced images according to one embodiment of the present disclosure. In this embodiment, sliced image 320 corresponds to a connector with insufficient insertion defect, and sliced image 340 corresponds to a normal connector. It is noteworthy that both of the sliced image 320 and the slice image 340 are vertically sliced. As shown in FIG. 3, press-fit pins 322, 342 are pressed into the PCB through-holes 324, 344 by applying mechanical force, and it is not easy to measure the insertion depth unless measuring the pin length in vertical slice.

In other words, when the inspection device 100 inspects insufficient insertion defect of the examining target 128, the processing unit 142 may control the slicing portion 154 to cut a vertical slice of the reconstructed volume so as to speed up the determination of insufficient insertion defect.

In some embodiments, the inspection portion 156 may use multiple vertical slices to evaluate solder quality of package component. For example, vertical slices represent solder thickness profile, and therefore the inspection portion 156 may use the thickness profile to extract proper features, such as gradient, curvature, shape descriptor, geometric characteristics and the like. With the features of the solder, it is possible to create some inspection rules for quality determination, so as to speed up the determination of solder quality. Hence, in one embodiment, the inspection portion 156 may output the inspection result to the output device 180, such as in sufficient solder, open defect, excessive solder, good solder or NG solder. In another embodiment, the sliced images are displayed on the output device 180 for visual determination of solder quality by examiner.

Figure 4A:
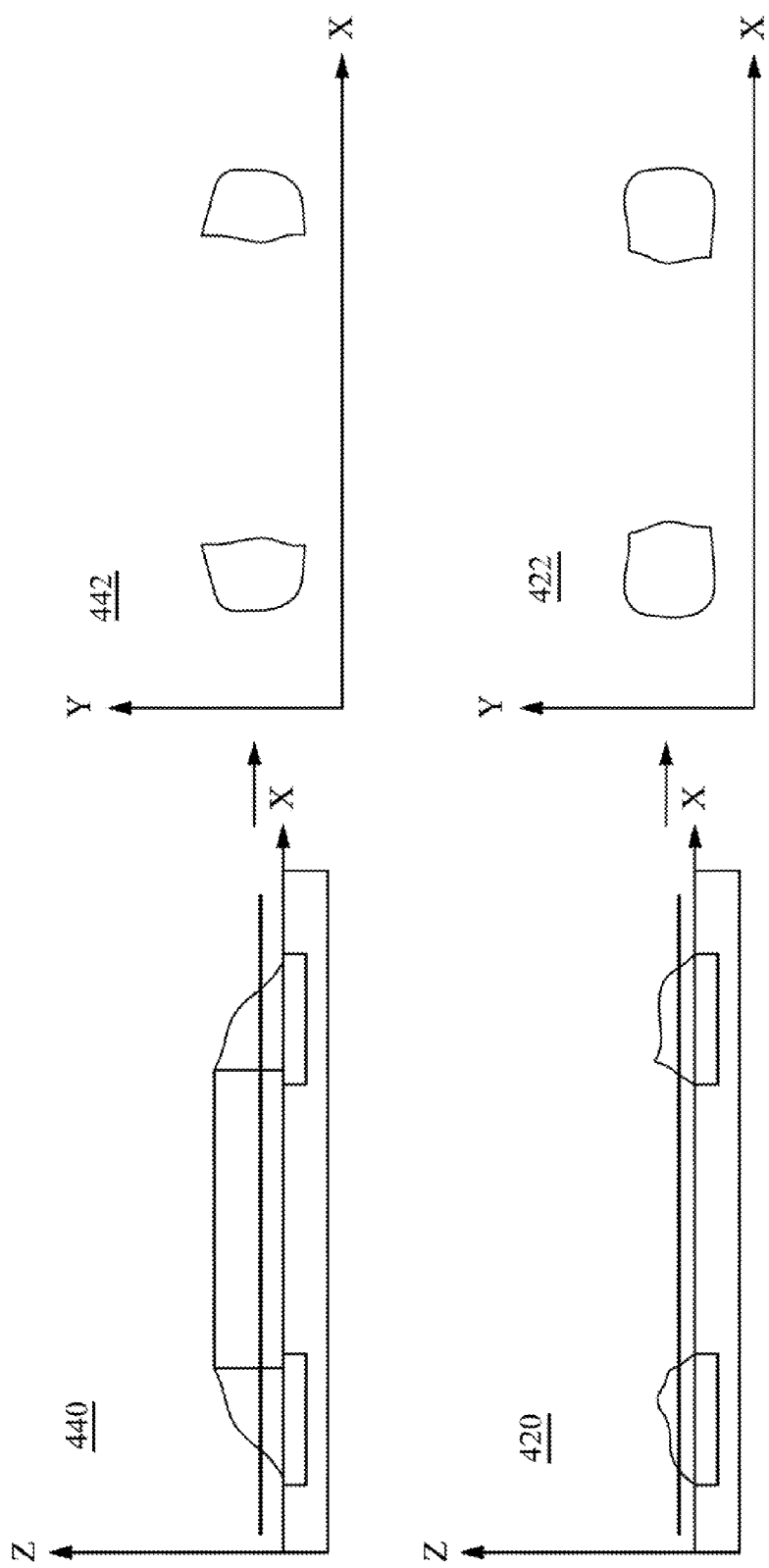
FIG. 4A is a schematic diagram illustrating reconstructed volumes and corresponding sliced images according to one embodiment of the present disclosure.

FIG. 4A is a schematic diagram illustrating reconstructed volumes and corresponding sliced images according to one embodiment of the present disclosure. In this embodiment, reconstructed volume 420 corresponds to a component with open defect, and reconstructed volume 440 corresponds to a component without open defect. In addition, sliced image 422 is the horizontal slice of the reconstructed volume 420, and sliced image 442 is the horizontal slice of the reconstructed volume 440.

As shown in FIG. 4A, it is hardly to detect open defect from normal examining target by only using the horizontal slice, such as the sliced image 422 and the sliced image 442, since there is no clue in the horizontal slice.

Figure 4B:
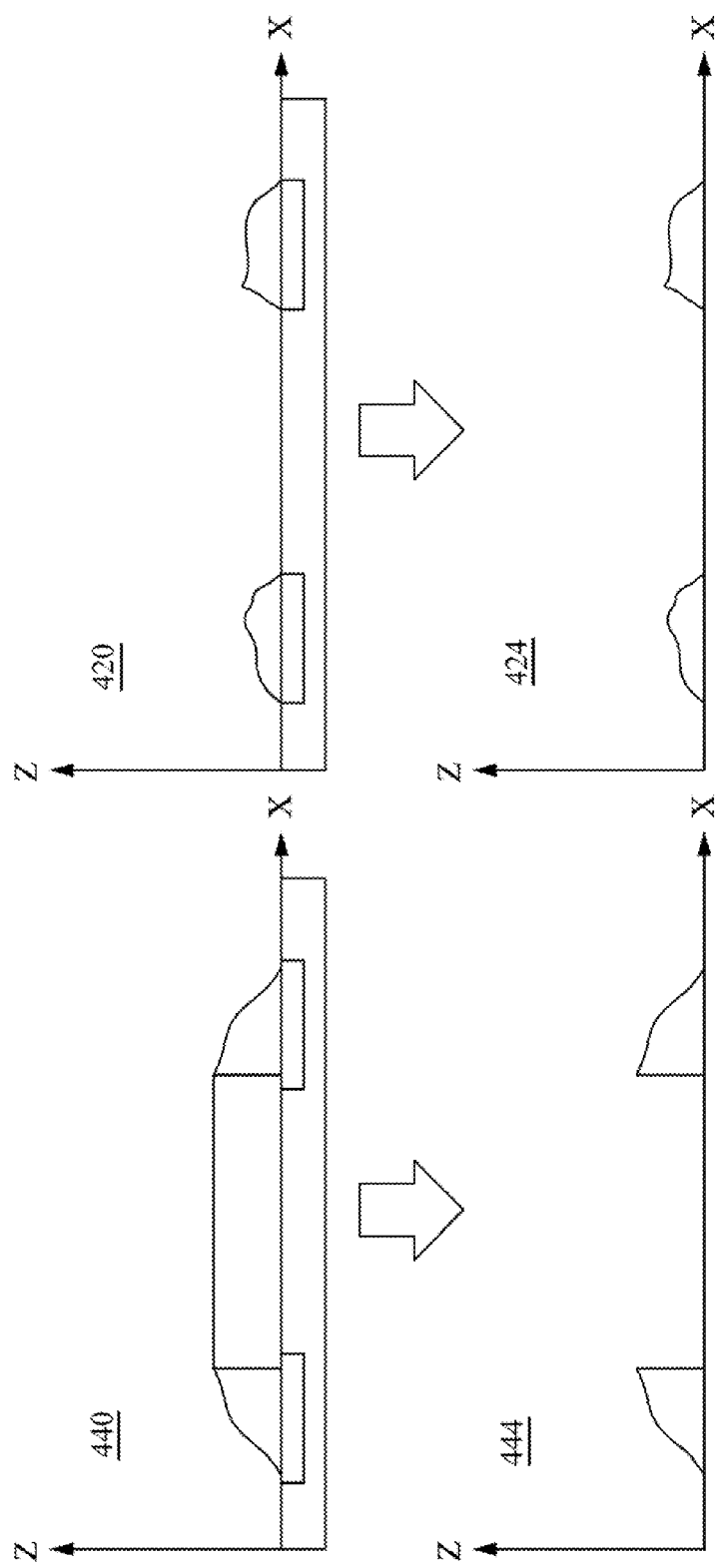
FIG. 4B is a schematic diagram illustrating reconstructed volumes and corresponding sliced images according to one embodiment of the present disclosure.

FIG. 4B is a schematic diagram illustrating reconstructed volumes and corresponding sliced images according to one embodiment of the present disclosure. In this embodiment, reconstructed volume 420 corresponds to a component with open defect, and reconstructed volume 440 corresponds to a component without open defect. In addition, sliced image 424 is the vertical slice of the reconstructed volume 420, and sliced image 444 is the vertical slice of the reconstructed volume 440.

For example, the inspection portion 156 may inspect open defect according to the shape of profile. As shown in FIG. 4B, if the shape is climbing from ground to the top like a hill, such as the edge of the sliced image 444, it means that the solder connects with the component well, and the open defect does not exist.

FIG. 5 is a schematic diagram illustrating a reconstructed volume and corresponding sliced images according to one embodiment of the present disclosure. In this embodiment, reconstructed volume 520 corresponds to a component with non-wetting open defect. In addition, sliced images 522A-

522C are the horizontal slices of the reconstructed volume 520, and sliced image 524 is the vertical slice of the reconstructed volume 520.

As shown in FIG. 5, there is no significant feature in the horizontal slices 522A-522C. Therefore, it is hard for the inspection portion 156 to determine non-wetting open defect according to the horizontal slices 522A-522C.

However, as shown in the sliced image 524, when non-wetting open defect occurs in the examining target 128, there are two blobs of solder on vertical cross section. Therefore, the inspection portion 156 may detect non-wetting open defect with solder connectivity feature by using the vertical slice. In other words, when the inspection device 100 inspects non-wetting open defect of the examining target 128, the processing unit 142 may control the slicing portion 154 to cut a vertical slice of the reconstructed volume so as to speed up the determination of non-wetting open defect.

Figure 6:
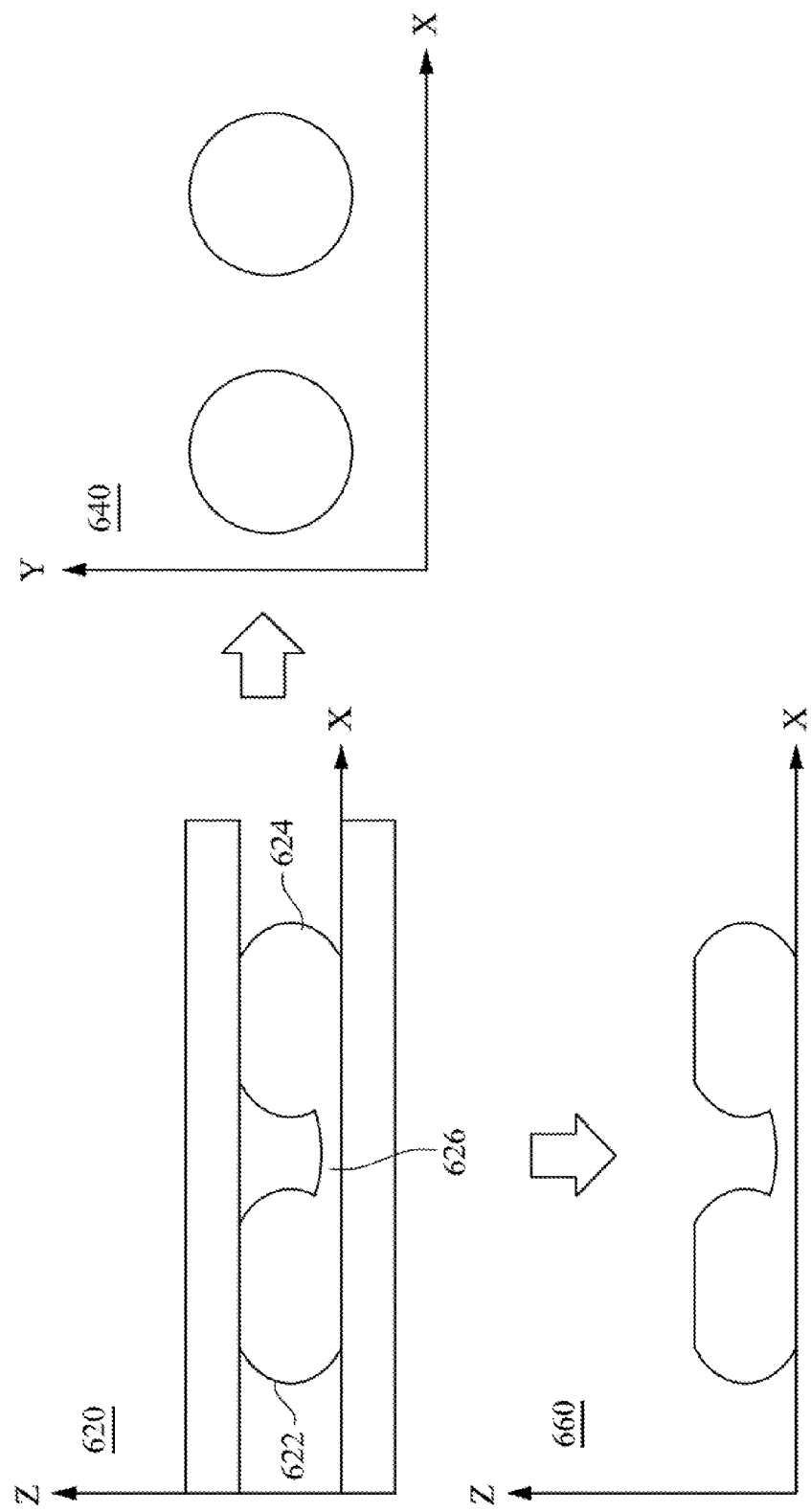
FIG. 6 is a schematic diagram illustrating a reconstructed volume and corresponding sliced images according to one embodiment of the present disclosure.

FIG. 6 is a schematic diagram illustrating a reconstructed volume and corresponding sliced images according to one embodiment of the present disclosure. In this embodiment, reconstructed volume 620 corresponds to a component with short defect. As shown in FIG. 6, solder ball 622 and solder ball 624 are shorted by redundant solder 626. In addition, sliced image 640 is the horizontal slice of the reconstructed volume 620, and sliced image 660 is the vertical slice of the reconstructed volume 620.

It is difficult to inspect the short defect by using horizontal slice, especially when the redundant solder 626 is not located in the same height with the solder ball 622 and the solder ball 624. However, vertical slice may directly reflect some significant features of short defect, so as to let the inspection portion 156 detect short defect successfully.

In some embodiments, the inspection device 100 further includes a drive mechanism 130 to transfer the examining target 128. Hence, the inspection portion 156 inspects the sliced image so as to detect whether the examining target 128 is abnormal in real time during the examining target 128 on drive mechanism 130.

Figure 7:
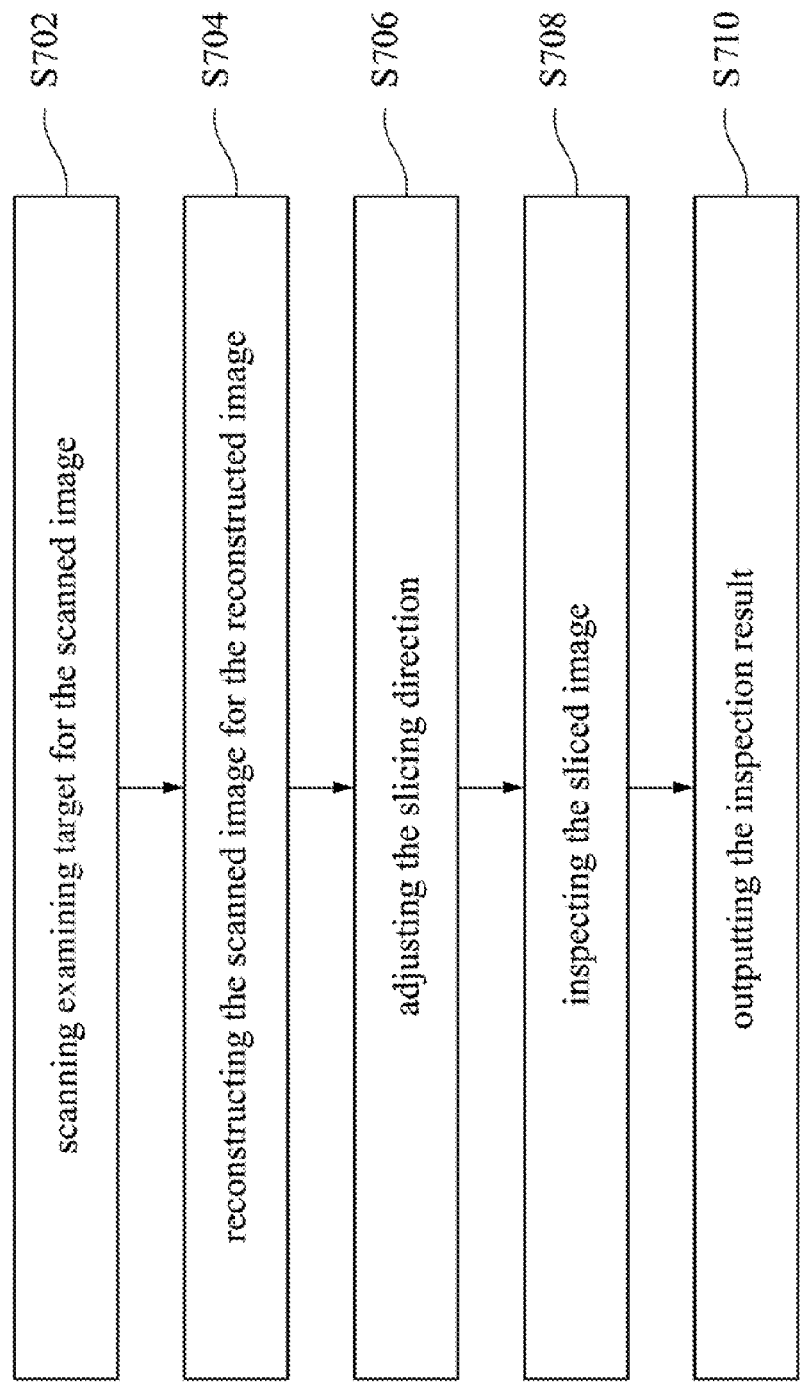
FIG. 7 is a flow chart of an inspection method according to one embodiment of the present disclosure.

Reference is now made to FIG. 7. FIG. 7 is a flow chart of an inspection method in accordance with one embodiment of the present disclosure. The inspection method may be implemented by the inspection device 100 illustrated in FIG. 1, but is not limited in this regard. For convenience and clarity, it is assumed that the inspection method is implemented by the inspection device 100 illustrated in FIG. 1.

In step 702, the scanning device 120 scans the examining target 128 so as to generate the scanned image. In step 704, the processing unit 142 controls the reconstruction portion 152 so as to reconstruct the reconstructed volume from the scanned image. In step 706, the processing unit 142 adjusts the slicing direction of the slicing portion 154 according to features of the examining target 128, so as to slice the reconstructed volume into the sliced image.

In step 708, the inspection portion 156 inspects the sliced image according to one or more features of the examining target 128 stored in the storage unit 144, so as to generate the inspection result of the examining target 128. In step 710, the computing device 140 outputs the inspection result of the examining target 128 to the output device 180.

By applying the techniques disclosed in the present disclosure, a non-horizontal slice of an examining target can provide some characteristics and significant features of the examining target. Therefore, the inspection performance may be improved and the inspection result may be more easily reviewed in repair station.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An inspection method, comprising:
   using a X-ray generator for generating X-ray to a printed circuit board (PCB);
   using a X-ray detector for detecting the X-ray transmitted through the PCB, so as to generate a scanned image of a solder of the PCB;
   reconstructing the scanned image for a reconstructed volume, wherein the step of reconstructing the scanned image for the reconstructed volume comprising is performed by using shift-and-add or computed tomography;
   adjusting a slicing direction associated with the solder of the PCB for slicing the reconstructed volume into a sliced image, wherein the slicing direction comprises a non-horizontal slicing direction;
   inspecting the sliced image for detecting whether the solder of the PCB has one or more defects in real time during a drive mechanism is transferring the PCB; and
   outputting an inspection result of the solder of the PCB.

2. The inspection method of claim 1, wherein the step of inspecting the sliced image and outputting the inspection result comprises:
   inspecting a symmetry of the sliced image; and
   outputting an abnormal result when the symmetry of the sliced image is under a predetermined threshold value.

3. The inspection method of claim 1, wherein the defects of the solder of the PCB comprise gradient, thickness, curvature, shape, or geometric characteristic.

4. The inspection method of claim 1, wherein the non-horizontal slicing direction is a vertical direction, and the defects of the solder of the PCB includes head in pillow (HIP), insufficient insertion, open defect, or non-wetting open defect.

5. The inspection method of claim 4, wherein the sliced image is hill-shaped when the solder of the PCB has no open defect.

6. The inspection method of claim 4, wherein the sliced image has two blobs when the solder of the PCB has non-wetting open defect.

7. The inspection method of claim 1, wherein the step of generating the scanned image is performed by using a line scan camera or a flat panel camera.

8. An inspection device, comprising:
   a X-ray generator configured for generating X-ray to a printed circuit board (PCB);
   a X-ray detector configured for detecting the X-ray transmitted through the PCB, so as to generate a scanned image of a solder of the PCB;
   a computing device connected with the scanning device, the computing device comprising:
   a processing unit configured to execute the following instructions:
      reconstructing the scanned image for a reconstructed volume, wherein the processing unit reconstructs the scanned image for the reconstructed volume by using a shift-and-add or computed tomography;

adjusting a slicing direction associated with the solder of the PCB for slicing the reconstructed volume into a sliced image, wherein the slicing direction comprises a non-horizontal slicing direction;

inspecting the sliced image for detecting whether the solder of the PCB has one or more defects in real time during a drive mechanism is transferring the PCB; and outputting an inspection result of the solder of the PCB;

a storage unit configured to store the scanned image, the reconstructed volume and the sliced image.

9. The inspection device of claim 8, wherein the processing unit is configured to inspect a symmetry of the sliced image and to output an abnormal result when the symmetry of the sliced image is under a predetermined threshold value.

10. The inspection device of claim 8, wherein the defects of the solder of the PCB comprise gradient, thickness, curvature, shape, or geometric characteristic.

11. The inspection device of claim 8, wherein the non-horizontal slicing direction is a vertical direction, and the defects of the solder of the PCB includes head in pillow (HIP), insufficient insertion, open defect, or non-wetting open defect.

12. The inspection device of claim 11, wherein the sliced image is hill-shaped when the solder of the PCB has no open defect.

13. The inspection device of claim 11, wherein the sliced image has two blobs when the solder of the PCB has non-wetting open defect.

14. The inspection device of claim 8, wherein the X-ray generator and the X-ray detector utilize a line scan camera or a flat panel camera to scan the solder of the PCB for generating the scanned image.

* * * * *